United States Patent [19]

Kastenhofer

[11] Patent Number: 5,467,873
[45] Date of Patent: Nov. 21, 1995

[54] BLISTER PACKAGING WITH SPRING MEANS THEREIN

[75] Inventor: Gerhard Kastenhofer, Effretikon, Switzerland

[73] Assignee: Schneider (Europe) A.G., Bulach, Switzerland

[21] Appl. No.: 217,396

[22] Filed: Mar. 24, 1994

[30] Foreign Application Priority Data

Jun. 18, 1993 [EP] European Pat. Off. ............ 93109814

[51] Int. Cl.⁶ ..................................... B65D 73/00
[52] U.S. Cl. ................ 206/363; 206/438; 206/461; 206/466; 206/471; 206/503
[58] Field of Search ......................... 206/497, 522, 206/461, 471, 524.8, 363, 438, 364, 439, 210, 207, 213.1, 466, 503

[56] References Cited

U.S. PATENT DOCUMENTS

| | | | |
|---|---|---|---|
| 2,745,545 | 5/1956 | Dunning | 206/466 |
| 3,104,172 | 9/1963 | Wizelman | 206/471 X |
| 3,148,772 | 9/1964 | Saffir | 206/210 |
| 3,198,327 | 8/1965 | Boehling et al. | 206/497 X |
| 3,202,280 | 8/1965 | Larson | 206/471 |
| 3,322,266 | 5/1967 | Lontz et al. | 206/205 |
| 3,335,850 | 8/1967 | Hertzberg | 206/497 |
| 3,966,045 | 6/1976 | Perdue | 206/461 X |
| 3,967,728 | 7/1976 | Gordon et al. | 206/364 |
| 4,050,576 | 9/1977 | Williams et al. | 206/210 |
| 4,434,893 | 3/1984 | Barlow | 206/522 |
| 4,597,765 | 7/1986 | Klatt | 206/205 X |
| 4,779,727 | 10/1988 | Taterka et al. | 206/364 |
| 4,890,739 | 1/1990 | Mize, Jr. et al. | 206/524.8 X |
| 5,044,495 | 9/1991 | Wyslotsky | 206/497 X |
| 5,105,942 | 4/1992 | Van Veen et al. | 206/364 |

FOREIGN PATENT DOCUMENTS

| | | | |
|---|---|---|---|
| 0724014 | 12/1965 | Canada | 206/522 |
| 0079198 | 7/1950 | Czechoslovakia | 206/461 |
| 1355790 | 2/1964 | France | 206/461 |
| 2131725 | 11/1972 | France . | |
| 2259015 | 8/1975 | France . | |
| 2266474 | 10/1975 | France . | |
| 2405872 | 5/1979 | France . | |

Primary Examiner—Bryon P. Gehman
Attorney, Agent, or Firm—Peter C. Richardson; Lawrence C. Akers; Philip C. Strassburger

[57] ABSTRACT

The packaging for a catheter comprises a flat air tight support member and a cover member formed of an air tight and flexible sheet adhered by its periphery on the support member. A vacuum is exerted between the support member and the cover member by connection of a duct to a vacuum pump, and the duct is then sealed. The cover member thus takes the relief of the shapes of the catheter whatever they are.

17 Claims, 3 Drawing Sheets

BLISTER PACKAGING WITH SPRING MEANS THEREIN

BACKGROUND OF THE INVENTION

This invention relates to a packaging to hold a product during storage and transit under controlled environmental conditions, said packaging comprising a support member having a rigid portion supporting the product and a cover member sealed on the support member to maintain the controlled conditions, said cover member being applied on the product and against the support member for housing the product and for securing it to the support member.

Packagings of that kind are made for example to protect sterile medical appliances against the risk of becoming unsterile and contaminated and to maintain the shapes of the appliance during storage and transit. They are generally made to whenever possible facilitate the packaging procedure as well as the unpacking of the medical appliance.

In some known packagings of this kind, the cover member is a molded plastic blister, the pressed-out or outwardly projecting portion of which corresponds to the shapes of the relief of the packaged product located on the support member. Upon its enclosing into the packaging, the medical appliance must be precisely and carefully introduced into the molding of the blister before sealing thereof onto the support member, and there is therefore some risk to damage delicate portions of the medical appliance, such as for instance preshaped tips of stems of catheters. Upon extraction of the medical appliance from the packaging, the blister must be unsealed and separated from the support member up to the level of a portion of the medical appliance which can be grasped by the doctor, and the blister can be then completely separated from the support member so that the doctor may fully extract the medical appliance. This is a delicate job because due to the hollow shape of the blister molding there can be some creasing or cuts of the blister or even some retention in the blister which can damage the medical appliance at the place where it is still in the blister. Apart from this problem, that kind of packaging is by no means universally usable because any blister molding is specific to one shape and there is needed as many blister moldings as there may be different shapes for the medical appliance.

U.S. Pat. No. 5,105,942 describes a blister packaging which comprises, in the pressed-out portion corresponding to the delicate pre-shaped stem of the medical appliance, a corrugated profile the purpose of which is to create some flexibility in the blister to avoid the risk of having that package portion creasing or buckling or tearing. This improvement does not eliminate, however, the need to carefully introduce the medical appliance into the blister molding and the need to carefully extract it therefrom in order to avoid damaging its delicate portions. And it does also not bring any solution to the absence of universality of the blister molding concept, because for every individual catheter curvature a special blister sheet has to be molded. A further problem with this packaging is the unpacking. In order that the tip curvature does not get deteriorated due to overbanding, the catheter has to be unpacked laterally from the blister. This means that the seal between the blister and the support has to be opened all way along the full length of the catheter. However, after the support is removed from the blister the sterile catheter is relatively unprotected against contamination. This is the case during the opening procedure and between the opening procedure and the actual release of the catheter for use in a medical procedure. This problem is eliminated by the packaging disclosed in EP 0440427. In this configuration the shaped tip curvature of the catheter is secured in a blister molded insert which is lengthwise movable in a tray. The tray together with the insert and the catheter that it contains is taken up in a sterile pouch. For unpacking, the pouch is opened only on its narrow side and the catheter can then be taken out lengthwise. The specific design of the tray and the insert and the relative movement of the insert to the tray ensure proper lateral unpacking of the delicate tip of the catheter without stress for the tip curvature. During opening of the package and between opening and actual release for use the pouch is protecting like an envelope the full length of the catheter against unintentional unsterile contamination. For this function this packaging needs a tray, an insert and additionally the pouch. The insert has to be molded with corresponding individual tooling for every single tip shape configuration.

A further development, described in the document PACK AKTUELL, No. 2/93, provides for a packaging made of a twofold inflatable plastic bag forming two chambers within which a product may be placed. Upon inflation of the twofold bag, the two chambers enclose the product as sort of a clamping cushion. To handle the chambers or clamping cushion with the enclosed product during storage or transit, there is needed an outer packaging or box. Of course, upon removal of the outer box and deflation of the twofold bag, there is absolutely no environmental or mechanical protection of the product.

SUMMARY OF THE INVENTION

The object of this invention is a highly versatile packaging which fits all the usual shapes of products, more particularly such as catheters and the like, and which permits to avoid damaging the product during the packaging procedure as well as during extraction thereof, that is simple to manufacture and easy to use, that is made of only few elements to produce less waste, and that protects the product against contamination even after the packaging is opened and prepared for release of the product.

To this effect, the packaging according to the invention complies with the definitions given in the claims.

In that way, whatever the shapes of the product, the flexible wall of the cover member takes the form of their relief over the support member immediately upon application of the said pressure medium, and the maintaining of the product is thus practically perfect. The packaging procedure of the product between the flexible wall of the cover member and the support member does not induce any risk of damaging the delicate parts of products such as catheters and the like because there is no need to preliminarily house them in a molding before sealing of the cover member. And the extraction of the product cannot generate any creasing or cut which could mark or otherwise damage its delicate portions during unsealing of the cover member and removal of the product because of the flexibility of the active wall of the cover member after release of the pressure, respectively after allowing access of atmospheric pressure.

The packaging according to the invention can be devised simply and economically. Hence, in case of a pressure exerted over the flexible wall that can be put out of shape, the said wall can be one of the walls of an inflated bag. In the case of a vacuum exerted between the flexible wall that can be put out of shape and the support member, the support member is air tight and the cover member can be devised as a simple air tight sheet which acts as the flexible wall that can be put out of shape.

To release the forces which are securing and maintaining the product in the packaging it is sufficient with the invention only to break the isolation that holds the pressure medium. Such breakage allows access or escape of the pressure medium and the pressure on the product is released. This can be done for example by breaking the seal of a vacuum bag. It is not important where along the length of the seal this is done. The effect will always be the same, the escape or access of the pressure medium. The position where the seal is designed to be broken up can therefore be selected where it is most convenient, for example the narrow side of a lengthy packaging. The product can then readily be grasped at one end and can be pulled out of the packaging. No complete uncovering of the product is necessary. During opening of the package and between opening and actual release for use the packaging is protecting like an envelope the full length of a product such as a catheter against unintentional unsterile contamination. Because the maintaining and securing forces are released through access or escape of the pressure medium, no lateral unpacking is necessary. This allows lengthwise removal of the product from a pouch, whereby the pouch in the invention is formed by the partly unsealed cover and the support member without the need of an additional envelope. The automatic release of all maintaining and securing forces after opening of the seal allows the construction of the support in only one piece because lateral unpacking by the help of a relative movement of two elements is no longer needed.

Since the positive pressure or the vacuum is contained in one single bag, the product can be prepared ready for use in one single simple and quick operation with no risk of contamination of the product through the person holding or opening the package.

The use of a metal foil for the packaging elements that are isolating the pressure medium allows an extremely resistant packaging with an extraordinary long shelf life. The use of an inflated bag to form the flexible wall allows the application of ethylene oxyd sterilization of the products. The support member can then be manufactured of a material that is permeable to gas but not permeable to bacteria. If a vacuum is used to generate the maintaining and securing forces for the product, a packaging can be designed that needs only two layers, namely the flexible wall and the support member. A lateral rim on a stiff support member or a gutter like support member facilitate stacking and handling of the packaging during storage and transit although the surface of the packaging might be deformed through the pressure medium. And a further interest is the fact that one of the elements forming the pouch not only protects the product after pressure release but at the same time also protects the product against mechanical damage.

The invention will now be described more particularly with reference to the accompanying drawings which show, by way of example only, five embodiments of the invention.

DETAILED DESCRIPTION OF THE INVENTION

Figure 1:
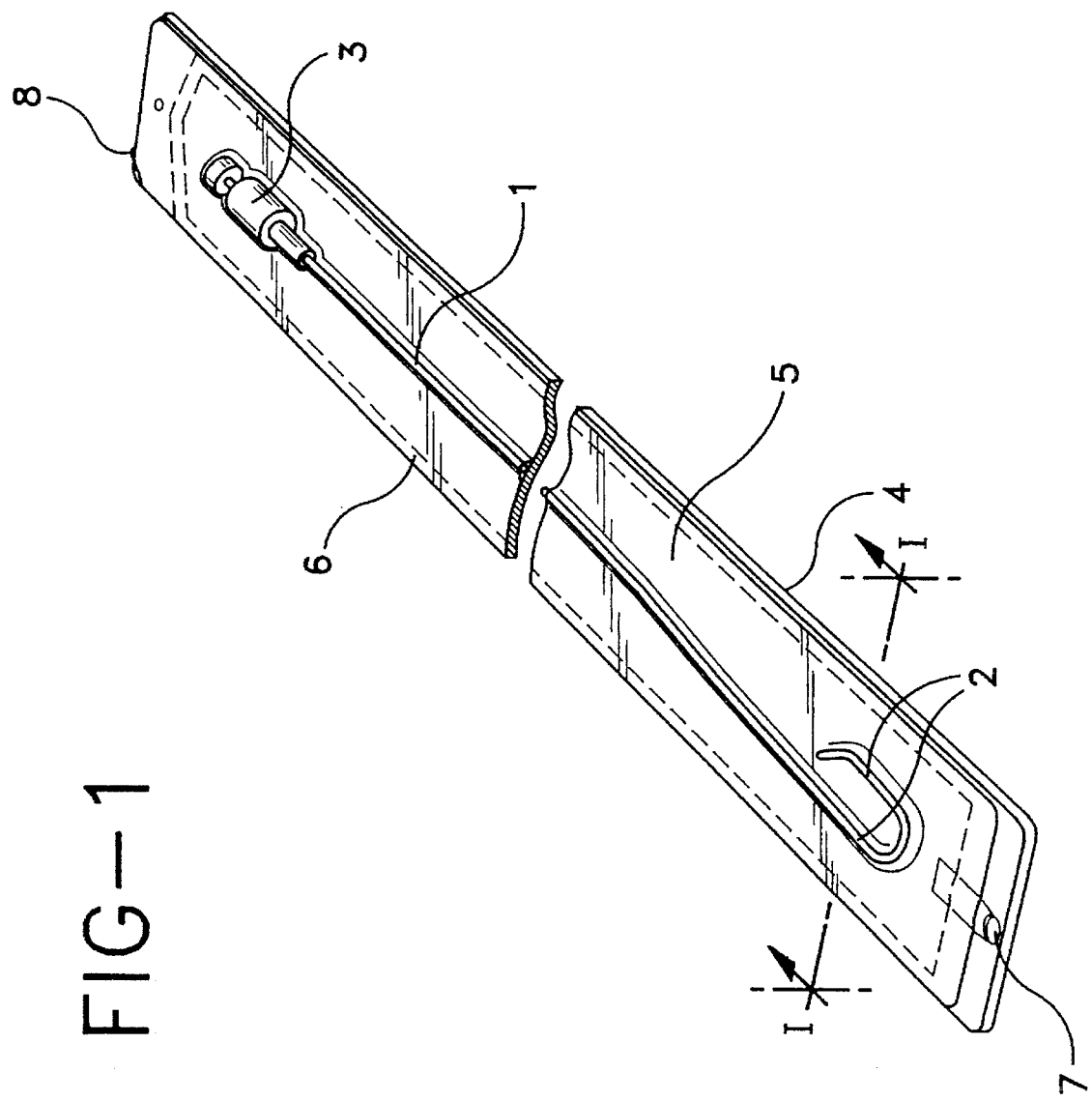
FIG. 1 is a general perspective view of the first embodiment.
Figure 2:
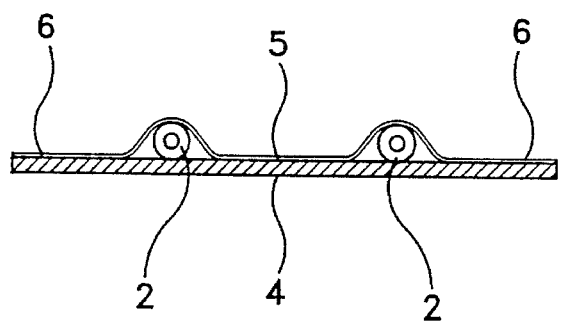
FIG. 2 is a transverse section according to line I—I of FIG. 1.

In the first embodiment of FIGS. 1 and 2 as well as in all the embodiments depicted in the drawings, the packaging is shown in the sterile storage condition of a medical appliance such as, for instance, a catheter comprising a stem 1 having at one end a pre-shaped tip 2 and at the other end a handling and/or connecting hub 3.

In the first embodiment, the packaging is composed of a flat support member 4 having a continuous and air tight surface, for instance an opaque plastic material, and a cover member 5 which is devised as a simple transparent plastic sheet which is flexible and which can be put out of shape; this sheet is also air tight and it is adhered to the support member 4 by heat sealing along a peripheral area 6 shown in dotted lines.

The stem 1, the pre-shaped tip 2 and the hub 3 of the catheter are firmly maintained on support member 4 and in their configuration by means of a vacuum exerted between the support member 4 and cover element 5. Upon enclosing of the catheter in the packaging, the vacuum is obtained for instance via a vacuum pump connected to a duct 7 affixed under the lower extremity of cover member 5, and this duct is then sealed by heat sealing on support member 4 before disconnecting the vacuum pump. In this embodiment, due to tightness of the support member 4 and of the cover member 5, the sterilization of the catheter may be obtained by gamma rays irradiation after sealing of the packaging.

Upon usage of the catheter, the nurse releases the vacuum by peeling back cover member 5, for instance by pulling on a tongue 8 purposely arranged at one of its top corners, and opens the packaging up to the level of the hub 3. The doctor may then grasp hub 3 and withdraw the catheter while the nurse holds the packaging open without touching the catheter.

In this first embodiment with a flat support member 4, the support member will be preferably sufficiently stiff to avoid the risk of deformation of the catheter during storage and transit.

Figure 3:
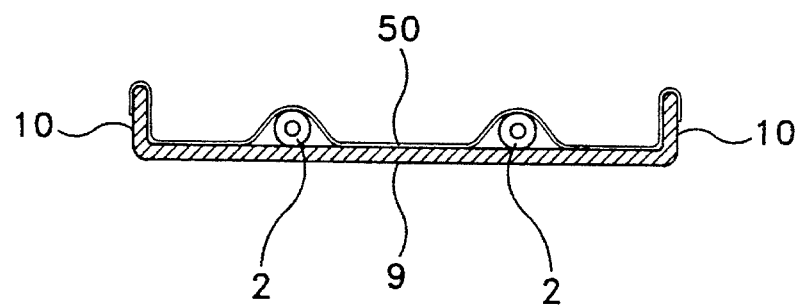
FIG. 3 is a transverse section of the second embodiment.

In the second embodiment shown in FIG. 3, such a stiffness is obtained by means of a support member forming a basis 9 with raised peripheral edges 10. The vacuum is also applied here between a cover member 50, formed by an air tight plastic sheet which is transparent and which can be put out of shape, and the support member 9 which is also air tight. The cover member 50 is adhered on the periphery of the support member 9, for instance by turning down and heat sealing on the upper part of the raised edges 10, the vacuum and unpacking being made as in the case of the first embodiment. This embodiment allows easy stacking of a series of packagings.

Figure 4:
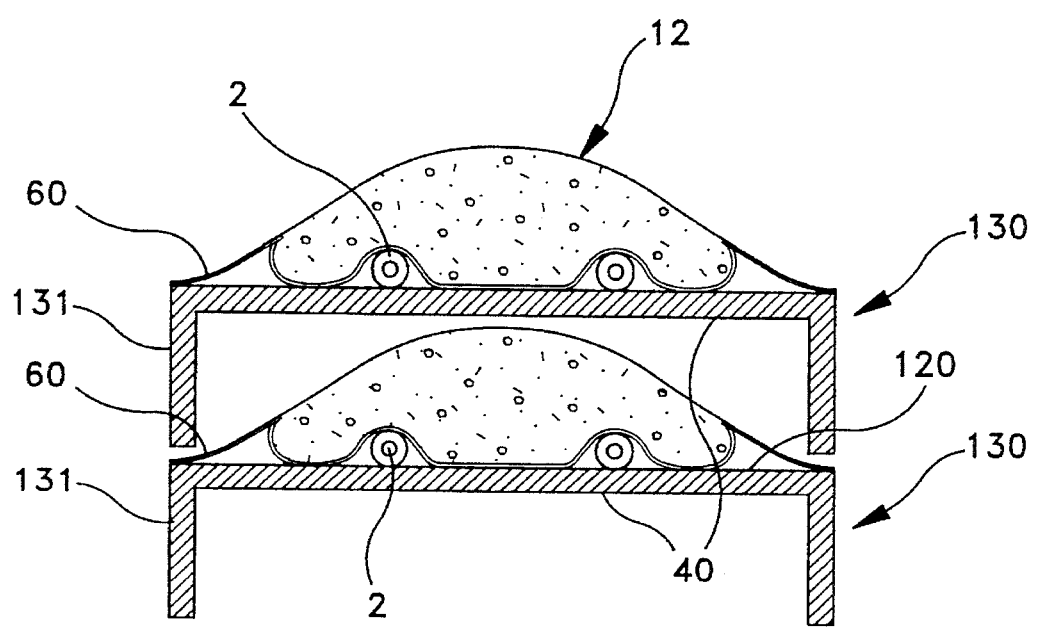
FIG. 4 is a transverse section of the third embodiment.

In the third embodiment of FIG. 4, air pressure is applied over the flexible wall of the cover member. The support member 130 is here formed of a basis 40 with downwardly extending lateral edges 131. The support member 130 is made of a porous material allowing chemical sterilization therethrough, for instance by means of ethylene oxyd. The cover member 12 is an air inflated transparent tight bag the lower wall 120 of which constitutes the flexible wall that can be put out of shape. The upper face of the bag 12 extends peripherally to form a border 60 which is adhered on the periphery of support basis 40 to assure the sealing of the packaging without affecting the sealing of the bag 12. Depending on the method used for adhering that border 60, the bag (12) forming the cover member may be inflated either before or after sealing thereof on support basis 40. Preferably, support basis 40 will be sufficiently stiff to accommodate possible stresses due to the deformation of the bag. As shown in FIG. 4, this embodiment also allows stacking of the packagings. In the fourth embodiment shown in FIG. 5, stiffness of the support member is obtained by means of a support member 90 with raised peripheral edges 10, as in the case of the second embodiment shown in FIG. 3. A transparent air inflated bag 121, the lower wall of which forms the flexible wall that can be put out of shape, is affixed to the raised edges 10 of support 90. In this embodiment, the upper wall of the cover member 121 may be stiffer than the flexible lower wall 122 to absorb the bulging resulting from the air pressure and to minimize the stresses on the raised edges 10. This embodiment is also adapted to chemical sterilization upon usage of a support member 90 made of a porous material.

Figure 5:
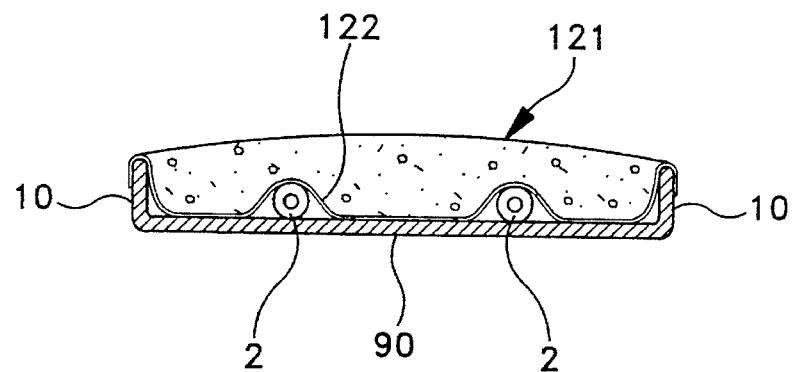
FIG. 5 is a transverse section of the fourth embodiment.

Upon usage of the catheter of the packaging according to the third and fourth embodiments as shown in FIGS. 4 and 5, the air inflated bag may be deflated for instance by mere pulling on a tongue (not shown) purposely arranged at one of its top corners. Another tongue can be connected to the lower wall of the inflated bag, to draw partly the bag from the support member.

Apart from the fact that the peeling of the first tongue releases a pressure, the unpacking procedure is thus substantially similar to that of the first and second embodiments.

In order to facilitate the pressure or vacuum release and withdrawal of the catheter, there may be provided to include spring means between the flexible wall of the cover member and the support member and on both sides of the medical appliance.

Figure 6:
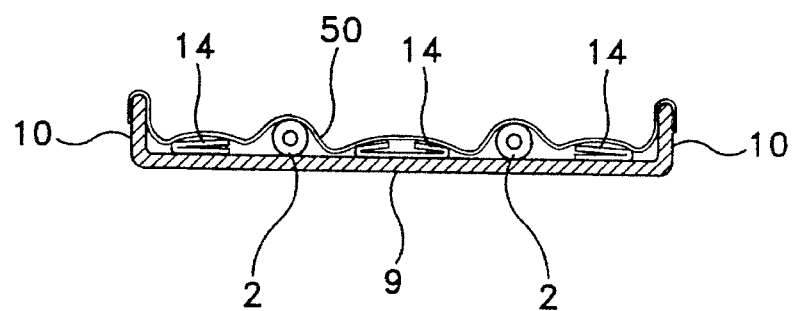
FIGS. 6 and 7 are transverse sections of the fifth embodiment respectively shown in two different conditions.
Figure 7:
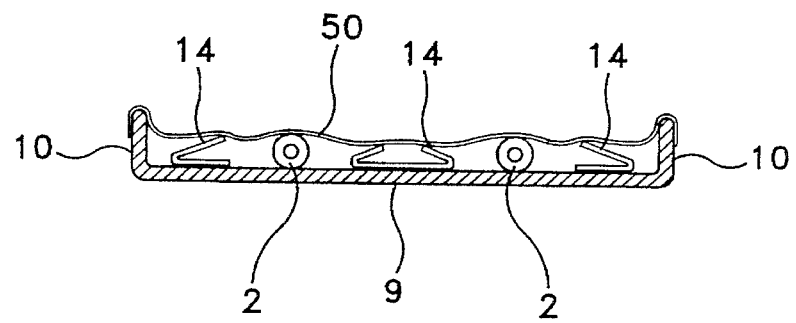

The fifth embodiment shown in FIGS. 6 and 7 incorporates such spring means within the environment of the packaging according to the second embodiment as shown in FIG. 3.

Such spring means may be constituted by V shaped resilient tongues 14, for instance of metal or folded cardboard; these tongues are visible in FIG. 6 in a compressed condition under flexible wall 50 which is subjected to a vacuum exerted between wall 50 and support member 9; the resilient tongues 14 are visible in depressed condition in FIG. 7 upon release of the vacuum between flexible wall 50 of the cover member and support member 9.

During the phase of vacuum release which occurs upon initiating the peeling back of cover member 50, the expansion of the resilient tongues 14 raises the cover member 50 and accelerates the air intake between cover member 50 and support member 9, thus facilitating withdrawal of the catheter. Such a spring action may also prove efficient in the first embodiment as shown in FIGS. 1 and 2 as well as in the other embodiments of FIGS. 4 and 5. Advantageously, the springs will be simply held in place on the support member by the mere pressure of the inflated bag on the support member as exemplified in the case of the vacuum exerted over the support member in FIG. 6.

Variants, not shown, may be considered within the frame of the invention.

Accordingly, in the first, second and fifth embodiments of FIGS. 1, 2, 3, 6 and 7, it is possible to avoid use of the duct 7 and connection thereof to a vacuum pump if the packaging procedure is made in a sterilized depression chamber.

According to another variant, the air inflated bags of the third and fourth embodiments may be inflated with a gas other than air. In addition, these inflated bags may be made of several juxtaposed and communicating chambers in order to reduce the bulging of the upper wall of the cover member resulting from the internal pressure of the system.

Still according to another variant, the basin shaped support member 9, respectively 90, of the second, fourth and fifth embodiments of FIGS. 3, 5, 6, and 7 may be replaced by a U shaped gutter like support member. In this case, adhering of the cover members 50, 121 on the support member may occur partly along the raised edges thereof and partly on the flat end portion located between the raised edges.

In all the embodiments shown, it is possible to make use of a metal foil for the elements which are isolating the pressure medium, in order to create an extremely resistant packaging with the resulting long shelf life, because other than plastic foils metal foil is virtually impermeable to gas.

I claim:

1. A package comprising:
   (a) a support member;
   (b) a cover member sealed to the support member to form an airtight chamber under pressure;
   (c) mechanical spring means disposed between the cover member and the support member for exerting force on each member, the mechanical spring means configured to maintain a separation between the support member and the cover member; and
   (d) a catheter disposed in the airtight chamber.

2. The package of claim 1 wherein the mechanical spring means is configured to maintain a separation between the support member and the cover member upon a decrease of the pressure.

3. The package of claim 2 wherein the support member has a rigid portion supporting the catheter, and wherein the cover member comprises a deformable flexible wall.

4. The package of claim 3 wherein the mechanical spring means is compressed by the flexible wall.

5. The package of claim 2 wherein the mechanical spring means is V-shaped.

6. The package of claim 5 wherein the mechanical spring means is made of cardboard.

7. The package of claim 2 wherein the support member has a peripheral rim configured to facilitate stacking of the package.

8. The package of claim 2 wherein the support member forms a U-shaped edge configured to facilitate stacking of the package.

9. The package of claim 2 wherein the pressure is a negative pressure.

10. The package of claim 2 wherein the pressure is a positive pressure.

11. A package comprising:
    (a) a support member;
    (b) a cover member sealed to the support member to form an airtight chamber under pressure; and
    (c) spring means disposed between the cover member and the support member for exerting force on each member, the spring means being V-shaped and configured to maintain a separation between the support member and the cover member.

12. The package of claim 11 wherein the spring means is made of cardboard.

13. A package comprising:
    (a) a support member forming a U-shaped edge configured to facilitate stacking of the package;

(b) a cover member sealed to the support member to form an airtight chamber under pressure; and (c) spring means disposed between the cover member and the support member for exerting force on each member, the spring means configured to maintain a separation between the support member and the cover member.

14. A package comprising:

(a) a support member;

(b) a cover member sealed to the support member to form an airtight chamber under pressure;

(c) V-shaped spring means disposed between the cover member and the support member for exerting force on each member, the V-shaped spring means configured to maintain a separation between the support member and the cover member upon a decrease of the pressure; and (d) a catheter disposed in the airtight chamber.

15. The package of claim 14 wherein the spring means is made of cardboard.

16. A package comprising:

(a) a support member forming a U-shaped edge configured to facilitate stacking of the package;

(b) a cover member sealed to the support member to form an airtight chamber under pressure;

(c) spring means disposed between the cover member and the support member for exerting force on each member, the spring means configured to maintain a separation between the support member and the cover member upon a decrease of the pressure; and (d) a catheter disposed in the airtight chamber.

17. A package comprising:

(a) a support member;

(b) a cover member sealed to the support member to form an airtight chamber under negative pressure;

(c) spring means disposed between the cover member and the support member for exerting force on each member, the spring means configured to maintain a separation between the support member and the cover member and (d) a catheter disposed in the airtight chamber.

* * * * *